(12) United States Patent
Traylor

(10) Patent No.: US 7,673,648 B1
(45) Date of Patent: Mar. 9, 2010

(54) AIR GAP WITH DEODORIZER APPARATUS AND METHOD OF USE

(76) Inventor: Paul L. Traylor, 2691 Richter, Suite 113, Irvine, CA (US) 92606

( * ) Notice: Subject to any disclaimer, the term of this patent is extended or adjusted under 35 U.S.C. 154(b) by 522 days.

(21) Appl. No.: 11/601,248

(22) Filed: Nov. 18, 2006

(51) Int. Cl.
*E03C 1/10* (2006.01)
(52) U.S. Cl. .................. 137/216; 261/DIG. 88
(58) Field of Classification Search ......... 137/215–218; 4/220, 228.1; 401/49, 56, 85; 261/DIG. 88; 422/120, 123; 239/44, 45, 47, 55, 57–59
See application file for complete search history.

(56) References Cited

U.S. PATENT DOCUMENTS

| 154,645 | A | * | 9/1874 | Chase ............................ 4/220 |
| 561,381 | A | * | 6/1896 | Ellis ............................... 4/220 |
| 4,984,307 | A | * | 1/1991 | Thomas ....................... 4/226.1 |
| 5,176,165 | A | | 1/1993 | Traylor |
| 5,240,653 | A | * | 8/1993 | Ramkissoon ................. 261/99 |
| 5,305,778 | A | | 4/1994 | Traylor |
| 5,592,964 | A | | 1/1997 | Traylor |
| 5,713,385 | A | | 2/1998 | Traylor |
| 5,915,406 | A | | 6/1999 | Traylor |
| 5,940,894 | A | * | 8/1999 | Cruz ............................. 4/222 |
| 6,453,931 | B1 | | 9/2002 | Traylor |
| 6,510,863 | B1 | | 1/2003 | Traylor |

* cited by examiner

*Primary Examiner*—John Rivell
*Assistant Examiner*—Craig M Schneider
(74) *Attorney, Agent, or Firm*—Mind Law Firm; Jeromye V. Sartain

(57) ABSTRACT

An air gap apparatus comprising a deodorizer agent positioned within the apparatus. The deodorizer agent may be any combination of a liquid, solid, granules or paste placed on or in a vent cap, an upper housing or upper housing cap of the air gap or receptacle thereon, a plugged inlet or inlet port extension extending from the air gap body, an under-mount nut or spacer installed on the air gap body, or an impregnation of or coating on any of the components thereof. With such an air gap installed for use, odors associated with bacterial growth within the air gap and discharged air passing through and out of the air gap are removed, disguised, offset or otherwise reduced or eliminated.

13 Claims, 4 Drawing Sheets

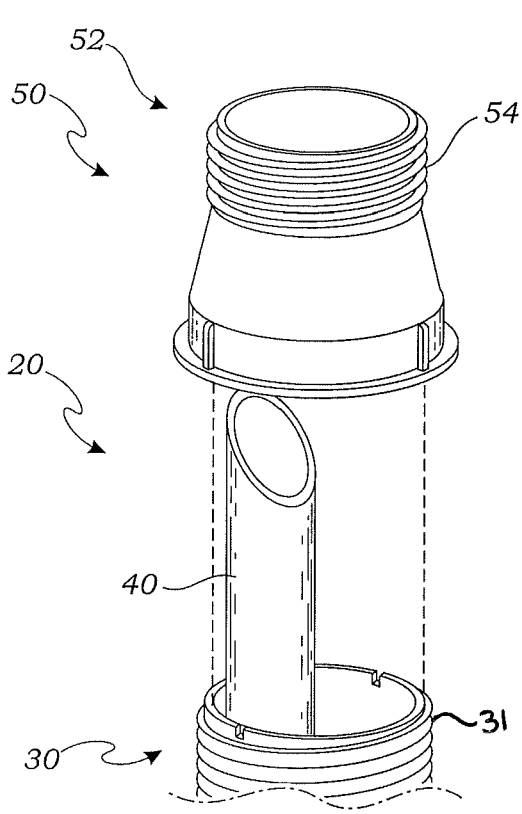
Fig. 1
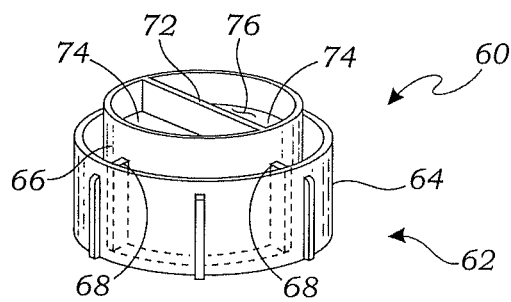
Fig. 2
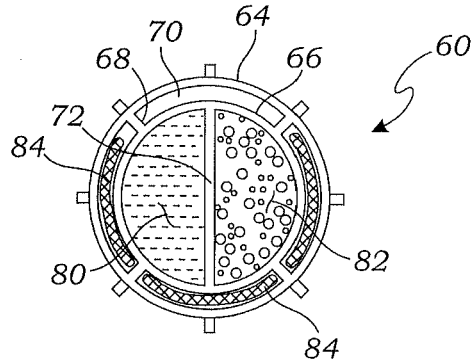
Fig. 3
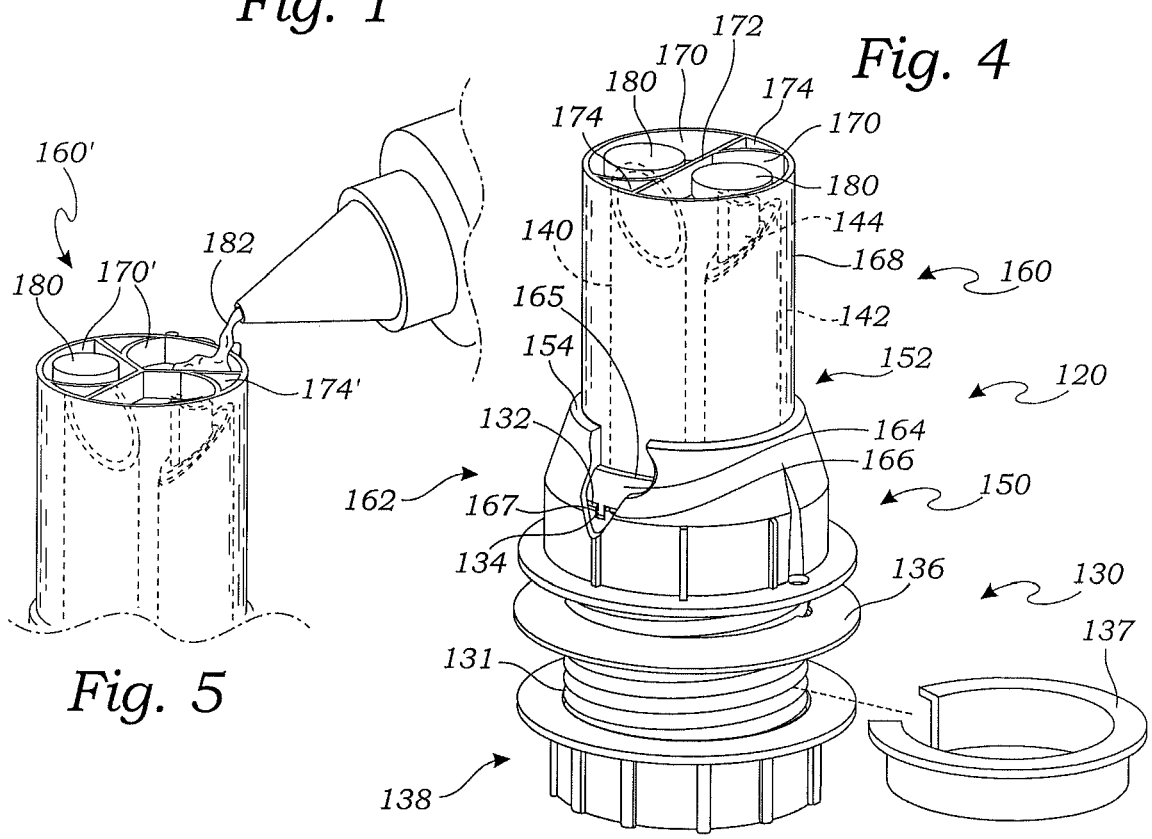
Fig. 4
Fig. 5

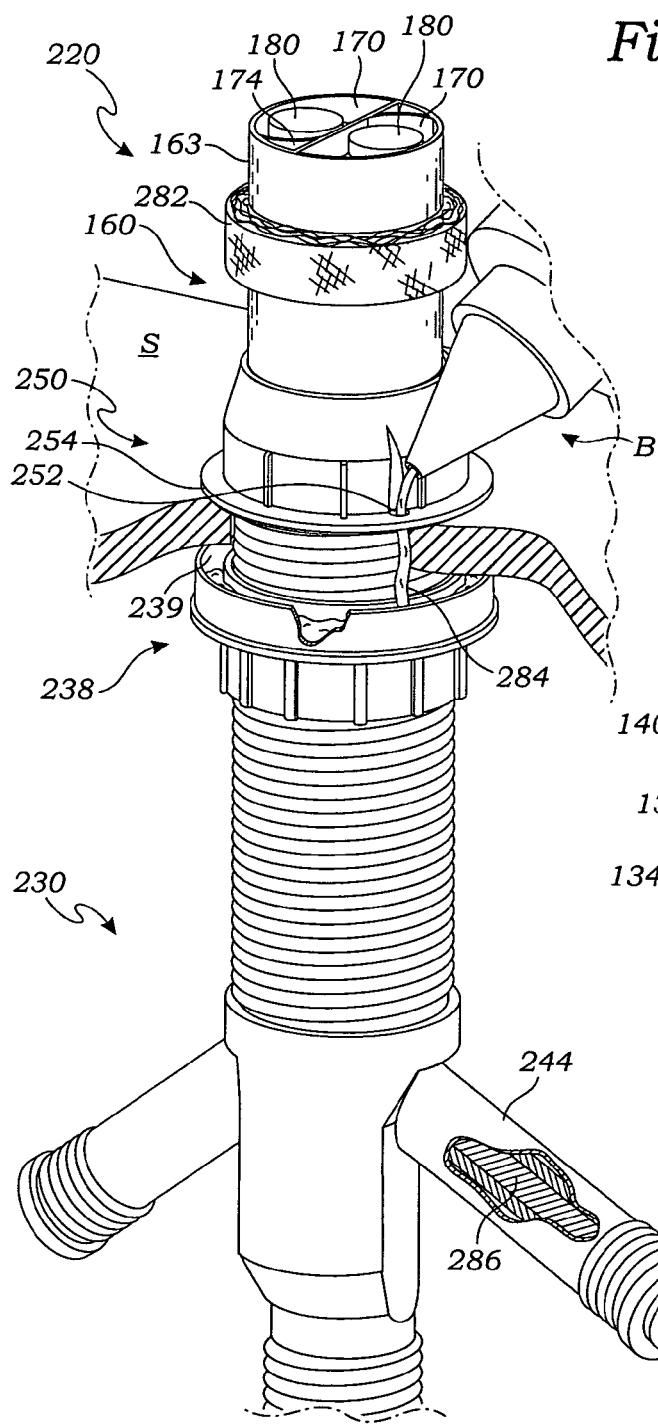
Fig. 6
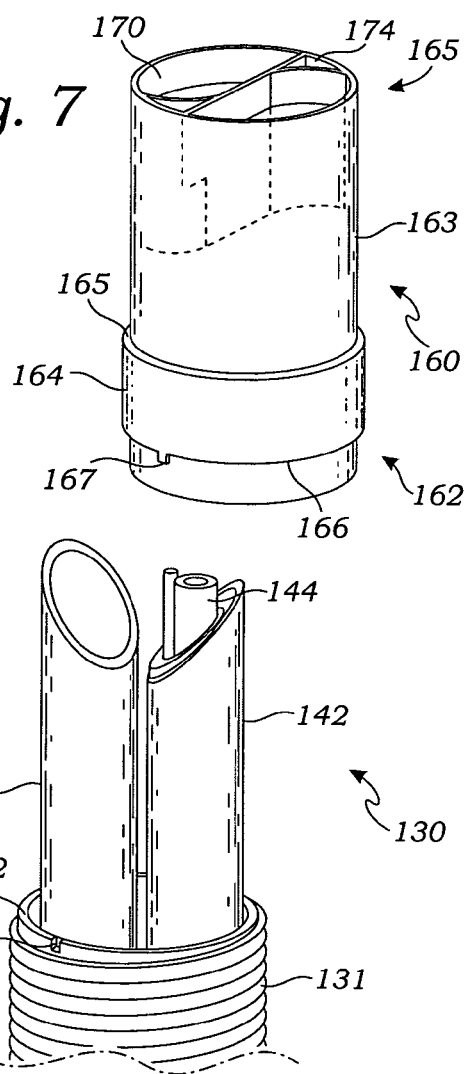
Fig. 7
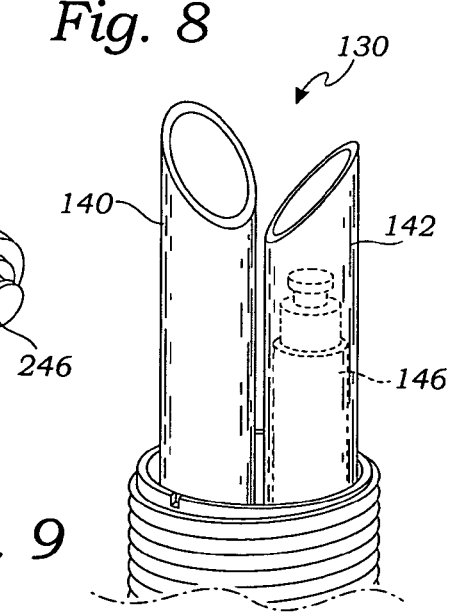
Fig. 8
Fig. 9

AIR GAP WITH DEODORIZER APPARATUS AND METHOD OF USE

INCORPORATION BY REFERENCE

Applicant hereby incorporates herein by reference any and all U.S. patents and U.S. patent applications cited or referred to in this application.

BACKGROUND OF THE INVENTION

1. Field of the Invention

Aspects of this invention relate generally to air gaps, and more particularly to air gaps configured with deodorizers.

2. Description of Related Art

Most plumbing codes specify that an anti-siphon device or air gap be provided to vent waste water discharge from household primary waste water sources such as dishwashers and the like. The air gap includes a vent chamber or space through which the waste water passes. This space is vented to atmosphere to prevent the establishment of a vacuum that could result in back siphoning of the contaminated dishwasher water back into the household water supply system. As is now known in the art, "single inlet" air gaps for venting the discharge from a dishwasher, for example, and "dual inlet" air gaps for venting the discharge from either a "two drawer" dishwasher or a standard dishwasher and another device such as a reverse osmosis ("RO") system, for example, are often employed.

Many prior art "single inlet" air gaps are capable of venting the waste water discharge from a single primary source such as a dishwasher or the like. One such single inlet air gap has come into such widespread use that it has become more or less standard in the trade. The air gap body is molded or otherwise formed of plastic material into a unitary or one-piece structure which includes a generally central leg constituting an outlet conduit or port that discharges all of the waste water coming from the air gap body into a household drain line for emptying into the sewer. The air gap body also includes a laterally divergent leg constituting a single inlet conduit or port through which waste water enters the air gap body.

The inlet port of the single inlet air gap body is clamped or otherwise attached to a dishwasher hose to receive the dishwasher waste flow and pass it to the air gap body. The discharge port of the air gap body empties all waste from the air gap body to a sewer pipe or the like via a household garbage disposer, if there is one, or directly to a household drain line connected to the sewer pipe.

Waste water entering through the inlet port from a dishwasher or from an RO drain line passes upwardly through the air gap body, where a flow diverter at the top of the body reverses the direction of waste flow downwardly through a space or spaces located interiorly of the air gap body for venting to the atmosphere. Such venting prevents development of a vacuum that might cause suction or back siphoning of the contaminated dishwasher water back into the household water supply system or the RO unit.

At least Applicant's U.S. Pat. Nos. 5,176,165, 5,305,778, 5,592,966, 5,713,385, 5,915,406, and 6,453,931 are representative of exemplary "single inlet" air gaps that may be employed in conjunction with the present invention.

By comparison, "dual inlet" air gaps, though otherwise much like their "single inlet" counterparts in general construction and use, include multiple inlets for a pair of dishwashers or dishwasher drawers and for an RO unit. All three of these inlets can be vented using an air gap having a pair of inlet ports for receiving multiple flows of waste water. At least Applicant's U.S. Pat. No. 6,510,863 is representative of exemplary "dual inlet" air gaps that may be employed in conjunction with the present invention, which air gaps are characterized by waste flow and venting passages whose rates of flow and dimensions are very close to those of the single inlet air gap presently in wide use, though this is not required and can vary depending on the application.

In such dual inlet air gaps, generally, the two or more inlet ports preferably each have an inner diameter essentially comparable to that of a single inlet air gap so that each of the inlet ports can handle the waste flow from one of the dishwasher drawers or from multiple other such producers of wastewater discharge. The dual inlet air gap is also typically configured to fit through the same standard sink opening that is provided for a single inlet air gap, to use the same hose fittings and other connections common to a single inlet air gap, and to adjust the venting spaces and passages to vent both discharges from the dual inlet air gap at a rate comparable to the specifications for a single inlet air gap. Specifically, the upper cap portion and cap vent or cover of such dual inlet air gaps have an overall size and configuration substantially equivalent to that of the standard single inlet air gaps.

It is known in the art that by virtue of the function of drainage air gaps, especially dishwasher air gaps, there frequently is an unpleasant odor that emanates from the cap vent opening(s). This odor likely is caused by one or more contributors: contaminated wastewater that is in the process of being discharged and so passes through the air gap body; by such wastewater lingering along surfaces of the air gap interior; by some bacterial growth in the warm and moist cap interior; or merely by virtue of the necessary exposure and venting of the wastewater discharge system and piping to the atmosphere in order for the air gap to perform as designed.

There is a need in the art for an air gap, whether single inlet, dual inlet, or some other configuration now known or later developed, capable of removing, disguising, offsetting or otherwise reducing or eliminating the unpleasant odors known to emanate from air gaps, and dishwasher air gaps in particular, during use, in the periods of a day or more between uses, and after use. Insofar as Applicant is aware, no such air gap is presently available. Aspects of the present invention fulfill these needs and provide further related advantages as described in the following summary.

SUMMARY OF THE INVENTION

Aspects of the present invention teach certain benefits in construction and use which give rise to the exemplary advantages described below.

Aspects of the present invention are generally directed to an air gap apparatus comprising a deodorizer agent positioned within the apparatus, whereby the unpleasant odors known to emanate from air gaps during and in between uses are removed, disguised, offset or otherwise reduced or eliminated.

Further aspects of the present invention are directed to an air gap having a removable vent cap, whereby the deodorizer agent is positioned underneath the vent cap.

Further aspects of the present invention are directed to an air gap body having an upper housing cap installed thereon configured with at least one compartment, whereby a deodorizer agent is placed in at least one of the compartments.

Still further aspects of the present invention are directed to an air gap body having an upper housing cap installed thereon and a ring mounted on the upper housing cap, whereby the ring includes a deodorizer agent.

Further aspects of the present invention are directed to an air gap in which the deodorizer agent is microscopic silver impregnated within or applied to one or more air gap surface.

Still further aspects of the present invention are directed to an air gap body having an inlet port extension extending from the body and a plug installed within the extension, whereby a deodorizer agent is contained in the extension.

Still further aspects of the present invention are directed to an air gap body configured with two inlets and a plug inserted within one of the two inlets so as to form a plugged inlet, whereby a deodorizer agent is contained in the plugged inlet.

Still further aspects of the present invention are directed to an under-mount nut installed on the air gap body substantially beneath the mounting surface for the air gap and configured with an upwardly-opening trough, and further aspects are directed to an upper housing installed on the body substantially above the mounting surface and configured with a vertical cross-hole, whereby a deodorizer agent is poured through the cross-hole into the trough.

Still further aspects of the present invention are directed to an upper housing installed on the air gap body substantially above the mounting surface, the upper housing being formed with an upwardly-opening circumferential channel, whereby a deodorizer agent is placed within the channel.

Still further aspects of the present invention are directed to an upper housing installed on the air gap body substantially above the mounting surface, the upper housing being configured with a cross-hole, and a spacer installed between the mounting surface and the upper housing and configured with an upwardly-opening trough, whereby a deodorizer agent is poured through the cross-hole into the trough.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 1 is a partial exploded perspective view of an exemplary embodiment of the invention;

FIG. 2 is a perspective view of an exemplary component of the invention comprising an air gap upper housing cap;

FIG. 3 is a top view thereof;

FIG. 4 is a partial perspective view, partially cut away, of an alternative exemplary embodiment of the invention;

FIG. 5 is a partial perspective view of an alternative exemplary embodiment of the invention;

FIG. 6 is a partial perspective view, partially cut away, of an alternative exemplary embodiment of the invention;

FIG. 7 is a perspective view of an alternative exemplary component of the invention comprising an air gap upper housing cap;

FIG. 8 is a partial perspective view of an exemplary component of the invention comprising an air gap body;

FIG. 9 is a partial perspective view of an alternative exemplary component of the invention comprising an air gap body;

DETAILED DESCRIPTION OF THE INVENTION

Figure 11:
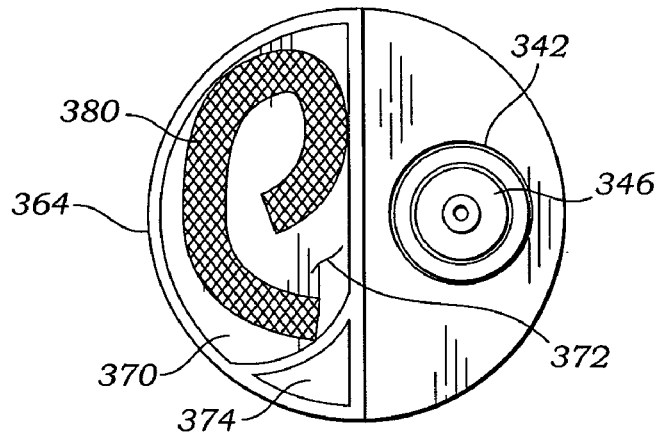
FIG. 11 is a partial top view thereof.

The above described drawing figures illustrate aspects of the invention in at least one of its exemplary embodiments, which are further defined in detail in the following description.

Referring first to FIG. 1, there is shown an exemplary single inlet air gap 20 having a body 30, an upwardly protruding inlet port extension 40 extending therefrom, and an upper housing 50 threadably installed on the body 30 so as to at least partially cover or enclose the inlet port extension 40 and to aid in installing the air gap within a hole formed in a sink or counter (not shown). Accordingly, the body 30 is formed with external threads 31 to engage the internal threads (not shown) of the upper housing 50. The upper housing 50 is configured at its top end 52 with an external thread 54. Referring now to FIG. 2, there is shown an upper housing cap 60 having on its bottom end 62 an internal thread (not shown) configured to threadably engage the external thread 54 of the upper housing 50. The upper housing cap 60 is thus able to be installed on the upper housing 50, which is itself threadably installed on the body 30, thus assembling the air gap 20 as one integral unit. It will be appreciated by those skilled in the art that the particular sizes, shapes and configurations of the components of the air gap 20 shown are merely exemplary and that numerous other components may be employed without departing from the spirit and scope of the invention. Specifically, it will be appreciated that the upper housing 50 may be tapered as shown or straight-walled, may be formed with various ribs or other features to facilitate manipulation, and though shown and described as having threads 54 at its top end 52 may instead be configured so as to be assembled with the upper housing cap 60 using any fastening means now known or later developed in the art for joining the upper housing 50 and the upper housing cap 60, including but not limited to tongue-and-groove snap-fit arrangements, press-fits, living hinge fasteners, mating shoulders or keys, and the like. It will be further appreciated that the upper housing 50 and upper housing cap 60 need not be separate components at all as shown in the exemplary embodiment, but in certain configurations may instead be formed as a single integral unit. In any event, each of the components comprising the air gap 20 may be formed from any suitable material and any suitable process now known or later developed, including but not limited to injection molded plastics. It is further contemplated that a microscopic silver may be incorporated into one or more of the components, whether in the molding or forming process or as a coating or the like in a secondary operation, as a further deodorizer and anti-bacterial agent. Relatedly, it will be appreciated that any material now known or later developed having anti-microbial or anti-bacterial properties may be permanently or temporarily applied to any of the surfaces of the air gap, particularly the wetted surfaces.

With continued reference to the exemplary embodiment of the air gap 20, and FIGS. 2 and 3, particularly, the upper housing cap 60 is formed so as to have a substantially annular outer wall 64 defining therein one or more upwardly-opening compartments 70, 74. In the exemplary embodiment of the upper housing cap 60 shown, a substantially annular inner wall 66 is formed radially inwardly offset from the outer wall 64 so as to be substantially concentric therewith. The two walls 64, 66 are connected to one another by one or more radial spokes 68 such that the spaces between adjacent spokes 68 and respective opposite portions of the walls 64, 66 define a first set of compartments 70. These compartments 70 may or may not have a bottom wall. Similarly, within the inner wall 66 there may be formed one or more partitions 72 to further divide that space into a second set of compartments 74. Again, these compartments 74 may or may not have a bottom wall. Those skilled in the art will appreciate that in the exemplary embodiment of FIGS. 1-3 at least one of the compartments 70, 74 should be formed without a bottom wall so that the air gap can breathe and function as designed in the art. Beyond this, the other compartments 70, 74 may be formed with a bottom wall 76 within the upper housing cap 60 so as to thereby contain a liquid, paste, granular, solid or other such perfume, deodorizer or other such agent as described more fully below. As used throughout, the terms perfume and deodorizer may be used interchangeably and are to each be understood broadly as a "catch-all" for any substance that emits a pleasant odor and/or masks an unpleasant odor, whether solid, liquid or gas, including materials that are known to have anti-microbial or anti-bacterial properties or effects. Even compartments 70, 74 not formed with a bottom wall may nevertheless contain a solid wick material such as a felt, as through an interference fit, which material may then be impregnated with or otherwise soak up a liquid perfume or the like. In the exemplary embodiment, at least one of the first set of compartments 70 is formed without a bottom wall and also does not house a wick material or the like so that the air gap 20 may breathe sufficiently. It will be appreciated by those skilled in the art that while a particular configuration of the upper housing cap 60 is shown and described as having four compartments defining the first set of compartments 70 between the outer and inner walls 64, 66 as set apart by a total of four spokes 68, and as having two compartments in the second set of compartments 74 as set apart within the inner wall 66 by a central partition 72 substantially along the diameter of the inner wall 66, with only the second set of compartments 74 having a bottom wall 76 so as to house liquid type agents while the compartments defining the first set of compartments 70 have no bottom wall and so house solid wick type materials in three of the four compartments 70, with the fourth being open-bottomed and not containing any material, the invention is not so limited. Rather, it will be appreciated that effectively an infinite variety of combinations of compartments having different sizes and shapes, some with floors and some without, are possible without departing from the spirit and scope of the invention. Those skilled in the art will further appreciate that even the outer and inner walls 64, 66 need not be annular, but may be of a variety of shapes to suit various applications. Accordingly, it is to be understood that the particular upper housing cap 60 shown and described is merely exemplary and only for illustration of the principles of the invention.

With continued reference to FIG. 3, it is shown that a liquid perfume agent 80 is poured or inserted into one of the two compartments comprising the second set of compartments 74, while in the other such compartment a perfume agent 82 configured as a paste or granules is inserted. In three of the four compartments comprising the first set of compartments 70 a solid perfume agent 84 is inserted. Once again, such a solid perfume agent 84 may be a felt, foam, open-cell or porous material, or any other such material that may be impregnated with or soak up a liquid type perfume, deodorizer, anti-bacterial composition, or other such liquid. To complete the assembly a vent cap (not shown) as known in the art is placed over the air gap 20 to conceal the upper housing 50 and upper housing cap 60 while enabling the air gap 20 to properly vent to the environment. It will be appreciated that, with such perfume agents 80, 82, 84 inserted in the upper housing cap 60, during installation and use of the air gap 20 of the present invention, air passing out of the air gap 20 as leaving the discharge line through the inlet port extension 40, then passing through one or more compartments of the upper housing cap 60, and finally finding its way out through the vent in the vent cap (not shown) to the atmosphere, the noxious or unpleasant odors that are typically associated with such discharged air are thereby removed, disguised, offset, or otherwise reduced or eliminated by the perfume agents 80, 82, 84. It will be appreciated by those skilled in the art that while some or all of the discharged air may pass directly over or immediately adjacent a perfume agent 80, 82, 84, leading to a direct exchange of matter or particles in the air, this is not necessary for the desired effect. Rather, the perfume agents 80, 82, 84 themselves will have an evaporative effect and essentially continuously release pleasant scents into the atmosphere, thereby masking the odors emanating from the discharged air from the air gap 20. However, in the case where the discharged air does pass directly over one or more of the perfume agents 80, 82, 84, it will be further appreciated that where these agents also contain anti-bacterial, anti-microbial or other such additives, the discharged air is not just disguised or offset but is effectively treated before it leaves the air gap 20. Ultimately, it is known in the art how perfumes, deodorizers, and the like function, and such is beyond the scope of the present invention. Those skilled in the art will instead appreciate that any number and kind of perfume agents may be employed in an air gap according to aspects of the present invention so as to reduce or eliminate the unpleasant odors often associated with the air discharged from an air gap. Accordingly, while a particular configuration of upper housing cap 60 filled with a particular variety of perfume agents so as to form a particular air discharge flow path relative thereto is shown, the invention is not so limited, and effectively an infinite variety of combinations of compartments and perfume agents may be employed without departing from the spirit and scope of the present invention.

Turning now to FIGS. 4 and 5, there are shown alternative exemplary embodiments of the air gap 120 of the present invention. In these embodiments, a dual inlet air gap 120 is employed having a body 130 configured with two substantially parallel inlet port extensions 140, 142. An upper housing 150 is threadably installed on the body 130. With reference to FIG. 4, the upper housing 150 is formed at its top end 152 with a radially inwardly projecting flange 154 configured to engage a raised circumferential band 164 formed near the bottom end 162 of the upper housing cap 160. Specifically, the top edge 165 of the band 164 engages the flange 154 while the bottom edge 166 of the band engages the top edge 132 of the body 130. That portion of the upper housing cap 160 below the band 164 seats within the inner lumen of the body 130. As such, it will be appreciated by those skilled in the art that once the upper housing cap 160 is positioned on the body 130 and the upper housing 150 is passed over the upper housing cap 160 and threadably tightened onto the body 130, the upper housing cap 160 is thus retained on the housing 130 with the band 164 effectively trapped between the top edge 132 of the body 130 and the flange 154 of the upper housing 150. One or more notches 134 may be formed in the upper edge 132 of the body 130 and a corresponding tab 167 formed so as to extend downwardly from the band 164 and engage one of the notches 134, whereby the correct orientation or alignment of the upper housing cap 160 relative to the body 130, and the inlet port extensions 140, 142, particularly, is achieved during assembly. While the second inlet port extension 142 is shown with an orifice insert 144 configured to affect the flow rate therethrough, as in the case where one of the discharge sources is an RO system operating at relatively low flow, it will be appreciated that the inclusion of this insert 144 is elective, not within the scope of the present invention, and is shown merely for illustration. The same can be said for the sealing ring or washer 136, the spacer washer 137, and the under-mount nut 138 also assembled on the body 130—these are merely illustrative and are beyond the scope of the invention.

With continued reference to FIGS. 4 and 5, the upper housing cap 160 is shown as having a substantially annular wall 168 terminating at its end opposite the band 164 in one or more compartments 170, 174, at least one of which not having a bottom wall so as to allow the air gap 120 to breathe from the inlet port extensions 140, 142 as above for the first exemplary embodiment air gap 20. In the exemplary embodiments of FIGS. 4 and 5, compartments 170 include a bottom wall so as to house solid or liquid perfume. Specifically, in FIG. 4, there are two such compartments 170 separated by a partition 172 and each containing a solid wafer perfume agent 180. Whereas, in FIG. 5, the upper housing cap 160' instead comprises three such compartments 170' configured with a bottom wall, with one again holding a wafer perfume agent 180, a second one instead filled with a liquid perfume agent 182, as from a bottle B or the like, and the third presently empty, though capable of holding another wafer, more liquid perfume agent, or any other such perfume or deodorizer. The liquid perfume agent 182 may be any perfume, deodorizer, anti-bacterial composition, or other such liquid. In either case, the opposite smaller compartments 174 are in these exemplary embodiments formed without bottom walls and do not contain any other kind of perfume agent so as to allow air to pass from the inlet port extensions 140, 142 therethrough and to vent to the atmosphere through the vent cap (not shown). Those skilled in the art will appreciate that with the simple removal of the vent cap to expose the upper housing cap 160, checking or adding to the perfume agents is easily accomplished. As previously, it will be further appreciated that any number of configurations of the air gap 120 and its components, and specifically the number and arrangement of compartments in the upper housing cap 160, as well as the types and quantities of perfume agents employed therein, are possible without departing from the spirit and scope of the invention, just as shown in the exemplary embodiments of FIGS. 4 and 5. Accordingly, it will be appreciated that the alternative exemplary embodiments shown and described are merely illustrative and that the invention is not so limited.

Referring now to FIG. 6, there is shown a further alternative exemplary embodiment of the air gap 220 of the present invention again including a dual inlet body 230 having the upper housing 250 threadably installed thereon so as to secure the upper housing cap 160 in position. Once more, the upper housing cap 160 is formed as in FIG. 4 with two compartments 170 with bottom walls so as to contain perfume agents in each, such as wafer perfume agents 180, with the opposite compartments 174 again venting to the atmosphere through the vent cap (not shown). In addition, there is also shown in this alternative embodiment three other perfume agent configurations that are possible within the spirit and scope of the invention. First, a solid wick material perfume agent is formed as a sleeve 282 that is slid over the outer wall 163 of the upper housing cap 160. The sleeve 282 may span virtually the entire exposed circumferential surface of the outer wall 163 or only a portion thereof and may be of virtually any thickness within the range between the outer wall 163 and the inside surface of the vent cap (not shown). Again, the wick sleeve perfume agent 282 may be formed from a felt, foam, open-cell or porous material, or any other such material that may be impregnated with or soak up a liquid type perfume, deodorizer, anti-bacterial composition, or other such liquid. A second further alternative perfume agent configuration included in the exemplary air gap 220 of FIG. 6 is shown as a liquid perfume agent 284 being poured from a bottle B into an upwardly-opening trough 239 formed in the under-mount nut 238. The liquid perfume agent 284 may also be any perfume, deodorizer, anti-bacterial composition, or other such liquid. The path to the trough 239 from above the mounting surface S is through a vertical cross-hole 252 formed substantially in the base 254 of the upper housing 250, with clearance then existing between the bore in the mounting surface S and the outside surface of the body 230 with the absence of a spacer washer, whereby there can be fluid communication between the cross-hole 252 and the trough 239. It will be appreciated that even where a standard spacer washer 137 (FIG. 4) is used, so long as the split in the washer 137 is oriented under or aligned with the cross-hole 252, the same result could be achieved. Finally, with continued reference to FIG. 6, a third alternative perfume agent configuration is shown as a solid stick 286 placed in one of the branches 244 of the dual inlet body 230. This would be case where such a dual inlet body 230 was installed but only one discharge source was to be accommodated. As such, the free lower end of the unused branch 244 of the body may be plugged with a plug 246. The stick perfume agent 286 could be placed into the branch from above by inserting it into the appropriate inlet port extension (not shown). Or, the stick perfume agent 286 can simply be inserted into the unused branch 244 before it is plugged. The stick may be significantly shorter than the entire length of the inlet port, may span such length, or could be any length in between, and can be made from a felt, foam, open-cell or porous material, or any other such material that may be impregnated with or soak up a liquid type perfume, deodorizer, anti-bacterial composition, or other such liquid. It will be appreciated by those skilled in the art that in some circumstances a liquid perfume agent could be poured into the plugged branch 244 through the appropriate inlet port extension (not shown). Those skilled in the art will appreciate that the evaporative effect of the perfume agents shown and described, whether placed on or about the upper housing cap 160, poured or placed in a trough 239 in the under-mount nut 238, or placed within a plugged, unused branch 244 of a dual inlet air gap body 230, will serve to mingle the perfume with the discharged air and thereby reduce or eliminate the unpleasant odors often associated with such air discharge from the air gap 220. Accordingly, once again, it will be appreciated that while exemplary forms of the components making up the air gap 220 and of the perfume agents and their locations within the air gap 220, the invention is not so limited. Rather, numerous other configurations and locations of the perfume agent on or about the air gap 220 are possible without departing from the spirit and scope of the present invention, so that the exemplary embodiments shown and described are to be understood as merely illustrative of aspects and principles of the invention.

Turning now to FIG. 7, there is shown a perspective view of the upper housing cap 160 of FIGS. 4 and 6. The annular outer wall 163 is once again shown as terminating in compartments 170, 174 at its top end 165 and having a raised circumferential band 164 formed near its opposite bottom end 162. The top edge 165 of the band 164 is configured to engage the flange 154 formed on the upper housing 150 (FIG. 4) while the bottom edge 166 of the band 164 is configured to engage the top edge 132 of the body 130 (FIGS. 4 and 8). The tab 167 extending downwardly from the band 164 and configured to mate with a corresponding notch 134 formed on the threaded end of the body 130 (FIGS. 4 and 8) is also clearly seen in this view.

Referring to FIG. 8, there is shown a perspective view of the exemplary "dual inlet" air gap body 130 of FIGS. 4 and 5. The body 130 again includes two substantially parallel inlet port extensions 140, 142 and external threads 131 to engage the internal threads (not shown) of the upper housing 150 (FIG. 4). One or more notches 134 are formed in the upper edge 132 of the body 130 and configured to engage the corresponding tab 167 (FIGS. 4 and 7) formed on the band 164, whereby the correct orientation or alignment of the upper housing cap 160 relative to the body 130, and the inlet port extensions 140, 142, particularly, is achieved during assembly of the air gap 120. Once more, the second inlet port extension 142 may have an orifice insert 144 inserted therein so as to affect the flow rate therethrough. By comparison, with reference now to FIG. 9, the same dual inlet air gap body 130 may have an inlet port extension 142 plugged, or have its flow rate restricted altogether, as by a plug 146. In this case, as where only one inlet of a dual inlet air gap 120 is needed for wastewater discharge, it will again be appreciated that the volume within the second inlet port extension 142 above the plug 146 may be used to hold a perfume agent, whether solid or liquid.

Figure 10:
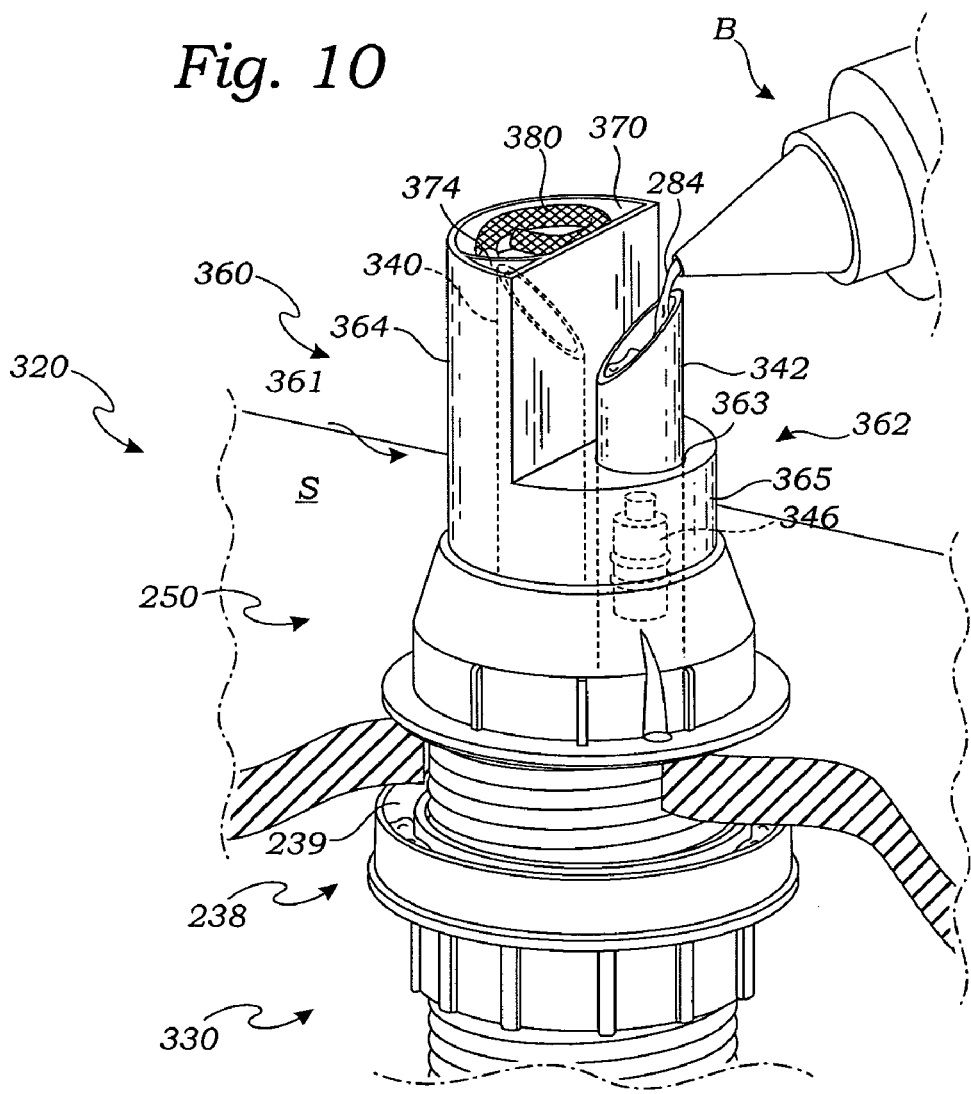
FIG. 10 is a partial perspective view of an alternative exemplary embodiment of the invention.

Turning to FIG. 10, while in the exemplary embodiment of FIG. 9 it will be appreciated that any of the above-described upper housing caps would have to be first threadably removed from the respective air gap body before any perfume agent could be added to the plugged inlet port extension, though it would be possible to also align such extension underneath a compartment of the upper housing cap not having a bottom wall and so have direct access to the plugged extension that way, an exemplary alternative approach, as shown, is to configure the upper housing cap 360 with essentially one half 361 having a full length so as to extend beyond and substantially cover the unplugged inlet port extension 340 and a second half 362 that is substantially shorter and configured with an opening 363 through which the plugged inlet port extension 342 is able to protrude. As such, those skilled in the art will appreciate that with the simple removal of the vent cap (not shown), direct access to the plugged inlet port extension 342 is achieved for the purpose of inspecting or adding to the perfume agent therein. With continued reference to FIG. 10, then, the alternative upper housing cap 360 is shown as being configured on its full half 361 with a substantially semicircular vertical wall 364 terminating in one or more compartments 370, 374. In the exemplary embodiment, as best shown in FIG. 11, the larger compartment 370 includes a bottom wall 372 so as to be able to hold any perfume agent. A solid wick type perfume agent 380 is shown, though it will be appreciated by those skilled in the art that any solid or liquid perfume agent could be placed in the compartment 370. The smaller compartment 374 has no bottom wall so as to enable venting of the air discharged from the unplugged inlet port extension 340. The adjacent shortened half 362 of the upper housing cap 360 is itself configured with a substantially semicircular wall 365 that extends only partway up the corresponding wall 364 of the full length half 361 of the cap 360. It will be appreciated that the length of the wall 365 will effectively be dictated in this embodiment by the length of the plugged inlet port extension 342. The plug 346 may be inserted into the inlet port extension 342 at really any point in the assembly and installation process of the air gap 320. Once the plug 346 is in place, again, the volume within the inlet port extension 342 above the plug 346 serves as a reservoir or compartment for a perfume agent. In the exemplary embodiment shown, a liquid perfume agent 284 is being poured from a bottle B into the plugged inlet port extension 342, though it will be appreciated that any solid or liquid perfume agent may be inserted therein within the scope of the invention. In addition to the perfume agents located in the larger compartment 370 formed in the top end of the longer or full half 361 of the upper housing cap 360 and in the plugged inlet port extension 342, there is also shown once again the use of a trough 239 formed in the nut 238 as a further container for a perfume agent. Those skilled in the art will appreciate that further perfume agents such as an appropriately sized wick ring about the continuous annular base portion of the cap 360, about the full half 361, and/or about the exposed outer portion of the plugged inlet port extension 342 are possible within the scope of the present invention. Ultimately, it will be appreciated that virtually any combination of the various perfume agents and corresponding geometries of the air gap, including the upper housing, upper housing cap and under-mount nut, are possible without departing from the spirit and scope of the invention. As such, it will be further appreciated that the additional alternative exemplary embodiments shown and described are merely illustrative and that the invention is not so limited.

Figure 12:
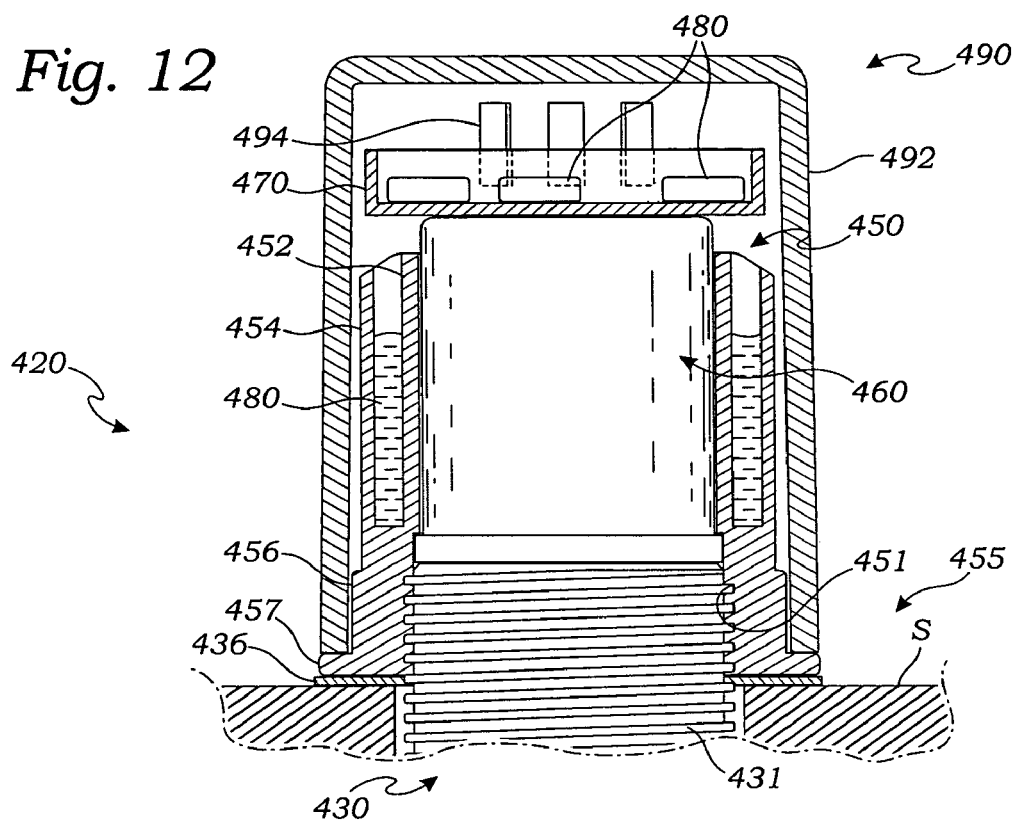
FIG. 12 is a partial cross-sectional view of an alternative exemplary embodiment of the invention.

Referring now to FIG. 12, there is shown a partial cross-sectional view of yet another alternative exemplary embodiment of the air gap 420 of the present invention. The upper housing 450 is threadably installed on the air gap body 430 so as to secure the upper housing cap 460 thereon. There is shown in FIG. 12 the engagement of the external threads 431 of the body 430 with the internal threads 451 of the upper housing 450. The cap 460, and particularly its one or more compartments (not shown), may be configured in any manner within the spirit and scope of the present invention, including any of those embodiments described above in connection with FIGS. 1-11. As yet a further reservoir for holding a perfume agent 480, an upwardly-opening circumferential channel 452 is formed in the annular wall 454 of the upper housing 450. While this channel 452 may span the entire circumference of the upper housing 450, it may also be divided by any number of ribs or partitions as well and may even comprise a series of bores spaced circumferentially about the upper housing 450 substantially parallel to its axis. Depending on the configuration of the channel 452 and other factors, the perfume agent 480 employed may be liquid as shown, a solid felt or other such wicking material, or anything in between such as a gel or paste. Those skilled in the art will thus appreciate that the channel 452 formed in the upper housing 450 may take a number of configurations beyond those shown and described without departing from the spirit and scope of the invention, including geometry that is not within the literal definition of "channel." As shown in FIG. 12, a sealing washer 436 may be installed about the threaded portion of the air gap body 430 between the upper housing 450 and the mounting surface S so as to provide a seal as is known in the art. The upper housing 450 is also formed substantially at its lower end 455 with a shoulder 456 terminating in a radially-outwardly extending flange 457 on which the vent cap 490 seats, or is removably inserted. The vent cap 490 includes a cap portion 492 having formed therein at least one vent 494. The vent cap 490 may otherwise be formed of any configuration and material, the substance of which is beyond the scope of the present invention. As previously, it will be appreciated by those skilled in the art numerous other configurations and locations of the perfume agent on or about the air gap 420 are possible without departing from the spirit and scope of the present invention, so that the present alternative exemplary embodiment shown and described is to be understood as merely illustrative of aspects and principles of the invention. By way of further example, then, with continued reference to FIG. 12, there is shown a further compartment or receptacle 470 for storage of a perfume agent 480 of any type placed therein, though a tablet or solid form is shown. It will be appreciated that the receptacle 470 is configured essentially as an upwardly-opening cup that is simply positioned on top of the upper housing cap 460 beneath the vent cap 490. It will be further appreciated that with the receptacle 470 sized as shown having an outside diameter roughly equal to or even greater than that of the upper housing cap 460 so as to be spaced slightly from the inside wall of the vent cap 490, the receptacle 470 may simply be placed or sat on the top surface of the upper housing cap 460 without any securement means whatsoever, though two-sided tape, Velcro®, a temporary adhesive, or any other such non-permanent securing or attachment device now known or later developed may be employed in further stabilizing the receptacle 470 atop the upper housing cap 460. Those skilled in the art will appreciate that such a receptacle 470 may be employed in accordance with the principles of the present invention to effectively deodorize the discharged air from a standard or "off the shelf" air gap 420 without any retrofitting or custom components whatsoever, having obvious "after market" benefits. It will be further appreciated that at the most in the alternative exemplary embodiment of the receptacle 470 of FIG. 12, perhaps a slightly taller vent cap 490 would be necessary to provide the required clearance between upper housing cap 460 and the vent cap 490 to accommodate the receptacle 470.

Figure 13:
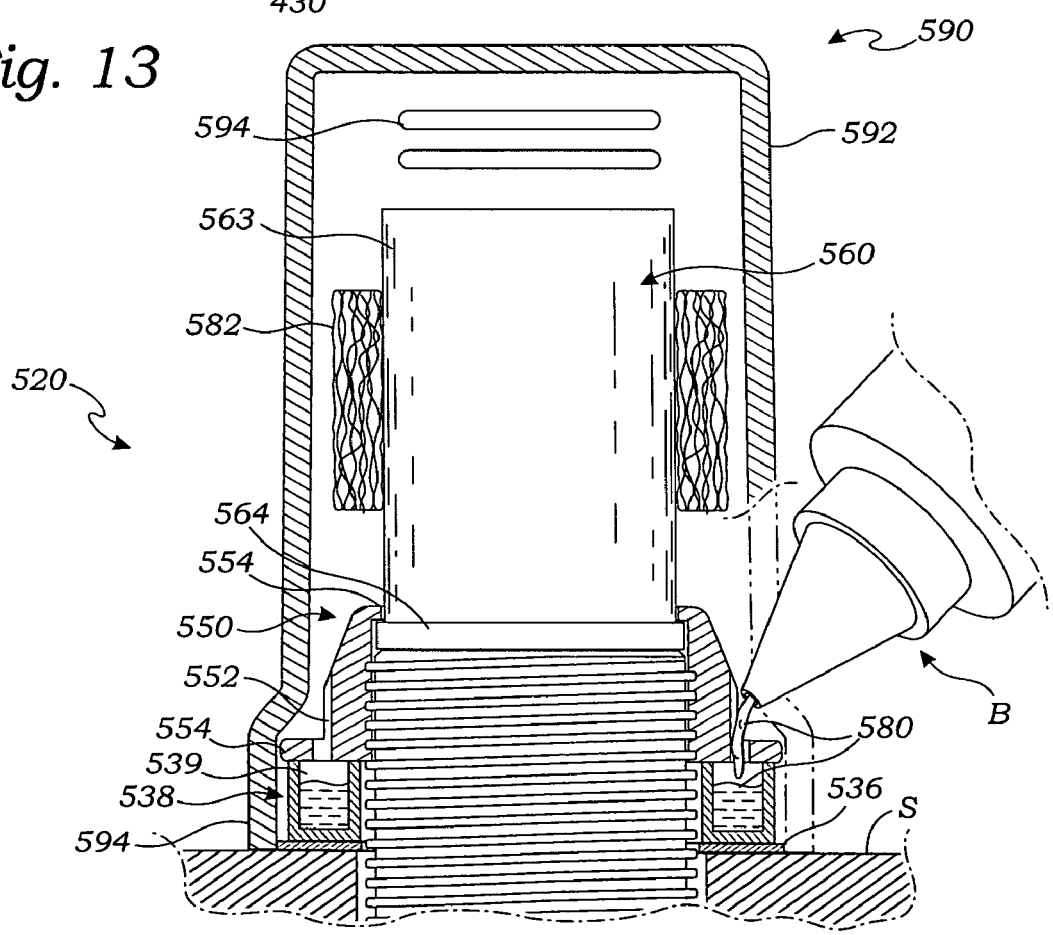
FIG. 13 is a partial cross-sectional view, partially cut away, of an alternative exemplary embodiment of the invention.

Finally, referring to FIG. 13, there is shown another cross-sectional view of yet one more alternative exemplary embodiment of the air gap 520 of the present invention. The upper housing 550 is again threadably installed on the air gap body 530 so as to secure the upper housing cap 560 thereon. There is clearly shown in FIG. 13 the engagement of the band 564 formed on the upper housing cap 560 with the radially inwardly projecting flange 554 formed on the upper housing 550 so as to secure the cap 560 in position. Once more, the cap 560, and particularly its one or more compartments (not shown), may be configured in any manner within the spirit and scope of the present invention, including any of those embodiments described above in connection with FIGS. 1-12. As yet a further reservoir for holding a perfume agent 580, a spacer 538 may be installed between the sealing ring 536 and the upper housing 550 and configured with an upwardly-opening trough 539 somewhat analogous to that of the under-mount nut 238 shown in FIG. 6. The trough 539 may hold a volume of liquid perfume agent 580, though can also hold other agents within the spirit and scope of the invention. As also analogous to the embodiment of FIG. 6, the upper housing 550 may be formed with one or more cross-holes 552 in its base 554 so as to allow fluid communication with the trough 539 while the air gap 520 is fully assembled, with only the vent cap 590 removed. For purposes of illustration only, the vent cap 590 is shown in FIG. 13 partially cut away to then illustrate the filling of the trough 539 through a cross-hole 552 with perfume agent 580 from a bottle B. A further solid wick or felt type perfume agent 582 is also shown as a ring that is formed or positioned about at least a portion of the outside surface 563 of the upper housing cap 560. Again, any combination of such perfume agents and/or compartments for housing such agents is possible without departing from the spirit and scope of the invention. Just as with the channel 452 of FIG. 12, the trough 539 need not be continuous about the circumference of the spacer 538, but may instead be separated by ribs or partitions for various reasons. Those skilled in the art will thus appreciate that the trough 539 formed in spacer 538 positioned below the upper housing 550 may take a number of configurations beyond those shown and described without departing from the spirit and scope of the invention, including geometry that is not within the literal definition of "trough." As shown in FIG. 13, the vent cap 590 not only includes a cap portion 592 having formed therein at least one vent 594, but also a flared base 594 so as to accommodate the spacer 538. The base 594 of the vent cap 590 then may seat against the washer 536, as shown, the outside wall of the spacer 538, and/or the outer edge of the flange 554 of the upper housing 550. The vent cap 590 may otherwise be formed of any configuration and material, the substance of which is beyond the scope of the present invention.

Based on the foregoing, it will be appreciated that virtually any combination of the various perfume agents and corresponding geometries of the air gap, including the upper housing and upper housing cap, are possible without departing from the spirit and scope of the invention. As such, it will be further appreciated that each of the alternative exemplary embodiments shown and described is merely illustrative and that the invention is not so limited. Moreover, while the various compartments, receptacles, troughs, or other such containers for the perfume agent as well as the sleeves and other such perfume agent rings are shown and described throughout as effectively being located under the air gap vent cap, it will be appreciated that for a variety of reasons any such structure may instead be incorporated on an outwardly-facing surface of any component of the air gap, including the upper body or the vent cap itself, without departing from the spirit and scope of the invention. It is to be expressly understood that any perfume agent now known or later developed, and whether a solid, a liquid, a semi-solid or a gas, may be employed in any of the exemplary embodiments shown and described or any other embodiments within the spirit and scope of the invention.

In use, as best illustrated by FIGS. 3-6 and 10-13, once an air gap according to the present invention is installed in a sink or countertop surface S via essentially any manner now known or later developed in the art, a perfume or deodorizer agent, again, in any form and whether or not incorporating anti-microbial, anti-bacterial or other such additives, may be added and monitored quickly and conveniently by essentially removing the air gap cover, or vent cap. Or, in alternative embodiments, such perfume agents may be monitored or replenished without even removing the vent cap. More specifically, in the exemplary embodiments, once the vent cap is removed to expose the upper body and upper body cap, as shown in all but FIGS. 12 and 13, in the case of solid and liquid perfume agents 80, 82, 84, 180, 182 added to upwardly-opening compartments 70, 74, 170 in the upper housing cap 60, 160, as in FIGS. 3-6, additional liquid perfume 80, 182 may be simply squirted or poured, as from a bottle B, into the desired compartment(s) 70, 74, 170 or onto a wicking material 84 placed within one or more such compartments. Similarly, solid perfume wafers 180 may be placed in selected compartment(s) as well. Upon replenishing the perfume agents, the air gap cover is then replaced over the air gap and deodorization of the discharged air and the air gap itself will continue indefinitely until the unit is again monitored and perfume agents further replenished as needed. Turning to FIG. 6, in the case where a solid wick material perfume agent is formed as a sleeve 282 that is slid over the outer wall 163 of the upper housing cap 160, just as for such a wicking material inserted within a compartment formed in the cap, a liquid perfume agent can be added to and absorbed into the sleeve 282 by simply squirting or pouring the liquid perfume onto the sleeve 282. Or, the sleeve 282 may be temporarily removed from the upper housing cap 160 and soaked in a liquid perfume agent and then replaced on the cap 160. Or, it is also possible that the sleeve 282 may be pre-impregnated with a perfume agent and would simply be discarded and replaced with another such sleeve 282 when necessary. It will be appreciated that other means now known or later developed of adding perfume agents to such wicking felt type materials that are then inserted on or within the air gap are possible without departing from the spirit and scope of the invention. Furthermore, with continued reference to FIG. 6, those skilled in the art will appreciate that when the air gap cover is removed to expose the upper portion of the air gap unit, the upper housing 250 and its cross-hole 252 are also exposed and accessible from above. Thus, as shown, a bottle B may be employed to dispense liquid perfume 284 through the cross-hole 252 and into the upwardly-opening trough 239 formed in the under-mount nut 238 as still a further means of deodorizing the discharged air and the air gap itself. Referring now to FIG. 10, in the event that one of the two inlets of a "dual inlet" air gap body 330 is not needed for any number of reasons, the appropriate inlet port extension 342 protruding upwardly from the body 330 may be plugged as with a plug 346 so as to form a compartment or receptacle for a perfume agent, which may then simply be added by pouring or placing such an agent into the extension 342 from its open, exposed end. As shown, liquid perfume 284 may be poured from a bottle B into the plugged extension 342 so as to again deodorize the air gap unit and any air discharged therefrom during or after use. As also shown in FIG. 10, other perfume agents, such as a solid wicking agent 380, for example, may also be added to one or more compartments 370 formed on the side of the upper housing cap 360 opposite the plugged extension 342. Those skilled in the art will thus appreciate from the foregoing that any combination of perfume agents and corresponding configurations of the air gap itself are possible without departing from the spirit and scope of the invention. Accordingly, in use, depending on the application and the kind or source of discharge passing through the air gap, a variety of combinations of perfume agents is possible in the present invention, by which the deodorization program and effect may be customized, again, to effectively meet the particular need. To reinforce this understanding of the present invention, two further examples of air gaps 420, 520 according to the present invention are illustrated in FIGS. 12 and 13 in use with the vent caps 490, 590 still on. In FIG. 12, with the vent cap 490 temporarily removed (not shown), a liquid perfume agent 480 has been added, once more, as by a bottle B (FIG. 13), for example, to the upwardly-opening channel 452 formed in the annular wall 454 of the upper housing 450. In the example of FIG. 13, such a liquid perfume agent 580 is instead added to the upwardly-opening trough 539 formed in the spacer 538 installed between the sealing ring 536 and the upper housing 550, the perfume 580 again passing into the trough 539 through the cross-hole 552 formed in the housing 550. In addition, a further solid wick or felt type perfume ring 582 is formed or positioned about at least a portion of the outside surface 563 of the upper housing cap 560, which ring 582 may again be replenished with perfume while still on the cap 560, by being removed, soaked and replaced, or simply by being discarded and replaced with a new perfume ring 582. Thus, it will be appreciated once more by those skilled in the art that a virtually infinite variety of configurations and uses of air gaps with deodorizers according to the present invention are possible without departing from its spirit and scope. In any such configuration, then, in use, it will be further appreciated that as air passes out of the air gap, as leaving the discharge line through one or more of the inlet port extensions, the air would then pass through one or more compartments of the upper housing cap and finally out through the vent in the vent cap to the atmosphere, the noxious or unpleasant odors that are typically associated with such discharged air are thereby removed, disguised, offset, or otherwise reduced or eliminated by the various perfume agents arranged in any combination as described above. Whether the discharged air passes directly over or immediately adjacent a perfume agent, leading to a direct exchange of matter or particles in the air, or the perfume evaporates into the air from the agents and so commingles with the discharged air as it vents, in either case, the perfume agents essentially continuously release pleasant scents into the atmosphere, thereby masking the odors emanating from the discharged air from the air gap. And where the discharged air does pass directly over one or more of the perfume agents, it will also be appreciated that if such agents also contain anti-bacterial, anti-microbial or other such additives, the discharged air is not just disguised or offset but is effectively treated before it leaves the air gap. As such, an air gap according to the present invention will continue to operate indefinitely until such time as one or more of the perfume agents are monitored and replenished or replaced as necessary as explained above.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor believes that the claimed subject matter is the invention.

What is claimed is:

1. A method of deodorizing an air gap apparatus, comprising the steps of:
    installing an air gap body having at least one hollow upwardly-protruding inlet port extension extending therefrom on a mounting surface; and
    pouring a liquid deodorizer agent into an at least one upwardly-opening, non-perforated compartment formed on an upper housing cap installed on an upper housing, the upper housing being installed on the body so as to at least partially cover the at least one inlet port extension and to aid in installing the air gap apparatus on the mounting surface.

2. The method of claim 1, comprising the further steps of:
    removing a vent cap removably installed on the body; and
    after the step of pouring the deodorizer agent, replacing the vent cap on the body.

3. The method of claim 1, comprising the further step of placing a wicking material on the upper housing cap.

4. The method of claim 3, comprising the further step of pouring an additional volume of liquid deodorizer agent onto the wicking material.

5. The method of claim 3,
    comprising the further steps of:
    removing the wicking material from the upper housing cap;
    soaking the wicking material in a liquid perfume; and
    replacing the wicking material on the upper housing cap.

6. An air gap apparatus comprising:
    a body having at least one hollow upwardly-protruding inlet port extension extending therefrom;
    an upper housing installed on the body so as to at least partially cover the at least one inlet port extension and to aid in installing the air gap apparatus within a hole;

an upper housing cap installed on the upper housing so as to form the air gap apparatus; and at least one substantially upwardly-opening, non-perforated compartment formed in the upper housing cap for containing a liquid deodorizer agent poured therein, whereby as discharged air passes out of the air gap apparatus through the at least one inlet port extension, the air then passes over the at least one compartment and the liquid deodorizer agent contained therein so as to effectively mask any unpleasant odors that are typically associated with such discharged air.

7. The apparatus of claim 1 wherein:

a band is formed on the upper housing cap;

the upper housing is formed with a radially inwardly projecting flange configured to engage the band; and the upper housing is installed on the body so as to secure the upper housing cap on the body.

8. The apparatus of claim 1 wherein:

the upper housing cap is formed on a top surface with at least two unitary, upwardly-opening, non-perforated compartments set apart by a partition.

9. The apparatus of claim 1 further comprising a vent cap, whereby the deodorizer agent is positioned underneath the vent cap.

10. The apparatus of claim 1 wherein the liquid deodorizer agent comprises at least one of an anti-microbial material and an anti-bacterial material.

11. The apparatus of claim 1 wherein the liquid deodorizer agent is further impregnated in a wicking material positioned on the upper housing cap.

12. The apparatus of claim 1 wherein:

the upper housing is installed on the body substantially above a mounting surface, the upper housing being configured with a cross-hole; and a spacer is installed between the mounting surface and the upper housing and configured with an upwardly-opening trough, whereby the deodorizer agent is poured through the cross-hole into the trough.

13. The apparatus of claim 12 further comprising a vent cap configured with a cap portion having at least one vent and further configured with a flared base so as to accommodate the spacer.

* * * * *

UNITED STATES PATENT AND TRADEMARK OFFICE
CERTIFICATE OF CORRECTION

PATENT NO. : 7,673,648 B1
APPLICATION NO. : 11/601248
DATED : March 9, 2010
INVENTOR(S) : Paul L. Traylor It is certified that error appears in the above-identified patent and that said Letters Patent is hereby corrected as shown below:

Column 15, lines 12 and 18, and column 16, lines 1, 4, 7 and 10, for the claim reference numeral "1", each occurrence, should read --6--.

Signed and Sealed this

Sixth Day of April, 2010

David J. Kappos
*Director of the United States Patent and Trademark Office*